United States Patent [19]
Doutremepuich et al.

[11] Patent Number: 5,922,358
[45] Date of Patent: Jul. 13, 1999

[54] ANTITHROMBOTIC AND NON-HEMORRHAGIC HEPARIN-BASED COMPOSITIONS, PROCESS FOR THEIR PREPARATION AND THERAPEUTIC APPLICATIONS

[75] Inventors: Christian Raymond Doutremepuich, Merignac; Francois Eugene Pierre Marie Saudubray, Bourdeaux, both of France

[73] Assignee: Debiopharm S.A., Switzerland

[21] Appl. No.: 08/793,314

[22] PCT Filed: May 29, 1995

[86] PCT No.: PCT/IB95/00405

§ 371 Date: Feb. 18, 1997

§ 102(e) Date: Feb. 18, 1997

[87] PCT Pub. No.: WO96/06623

PCT Pub. Date: Mar. 7, 1996

[30] Foreign Application Priority Data

Aug. 29, 1994 [FR] France .................................. 94/10380

[51] Int. Cl.$^6$ ........................ A61K 35/407; A01N 43/04; C08B 37/10
[52] U.S. Cl. ................................ 424/553; 514/56; 536/21
[58] Field of Search ...................... 424/520, 553, 424/557; 435/184, 212, 218, 195; 514/56, 54, 23; 536/21

[56] References Cited

U.S. PATENT DOCUMENTS

| | | | |
|---|---|---|---|
| 4,175,182 | 11/1979 | Schmer | 536/21 |
| 4,438,108 | 3/1984 | Sanders et al. | 424/183 |
| 4,687,765 | 8/1987 | Vairel et al. | 514/56 |
| 4,800,016 | 1/1989 | Yang | 210/206 |

OTHER PUBLICATIONS

Chargraff et al. "Studies on the chemistry of blood coagulation. VI. Studies on the action of heparin and other anticoagulatns. The influence of protamine on the anticoagulant effect in vivo" J. Biol. Chem. (1937) 122: 153–167.

Shanberge et al. "Heparin–protamine complexes in the production of heparin rebound and other complication of extracorporeal bypass procedures," Amer. J. Clin. Pathol. (1987) 87: 210–217.

Mannarino et al. "Efficacy of low–molecular weight heparin in the management of intermittent claudication", Angiology (1991) 42(1): 1–7.

Walsh et al. "Heparin and heparan sulphate are inhibitors of human leucocyte elastase", Clinical Sci. (1991) 81(3): 341–346.

Barkagan et al. "Determination of heparin in serum", Lab. Delo (1971) 6: 331–5; abstract only.

Doutremepuich et al. "Protamine neutralization of a very low molecular weight heparin fragment CY 222 in vitro and in vivo study", Thrombosis Res. (1986) Suppl. VI, p. 88; absytract only.

Sugiuama et al. "Study on neutralization of low molecular weight heparin (LHG) by protamine sulfate and its neutralization characterisitics", (1992) Thrombosis Res. 68: 119–129.

Lafuma et al. "Prevention of leucocyte elastase–induced emphysema in mice by heparin fragments", Eur. Respir. J. (1991) 4: 1004–1009.

Patent Abstracts of Japan vol. 4, No. 77, Jun. 4, 1980 & JP–A–55 043123 (Amano Pharmaceut. Co.Ltr.) Mar. 26, 1980.

*Primary Examiner*—Jean C. Witz
*Assistant Examiner*—Susan Hanley
*Attorney, Agent, or Firm*—Bierman, Muserlian and Lucas

[57] ABSTRACT

Heparin compositions having an antithrombotic activity and virtually no hemorrhagic activity are presented. The object of the invention is to eliminate the risk of bleeding associated with heparins while retaining their main properties. The compositions of the invention (S1, S2, S3) therefore consist of heparin moieties such as those obtainable by the in vitro neutralization of a heparin with a protamine. The invention also concerns a method for the preparation of these compositions which are useful in preparing medicaments.

22 Claims, 1 Drawing Sheet

ANTITHROMBOTIC AND NON-HEMORRHAGIC HEPARIN-BASED COMPOSITIONS, PROCESS FOR THEIR PREPARATION AND THERAPEUTIC APPLICATIONS

The present invention relates to heparin-based compositions as well as to a process for their preparation and to their therapeutic applications.

The invention relates more particularly to heparin-based compositions neutralized with protamine, having antithrombotic activity but largely devoid of haemorrhagic and anticoagulant activities.

Heparins have been known and used for many decades for the preparation of medicaments with antithrombotic and/or anticoagulant activity intended in particular for the preventive and curative treatment of venous and arterial thromboses or alternatively for preventing the activation of coagulation in extracorporeal circulations.

It has for many years been known how to prepare low molecular weight heparins, which always have antithrombotic activity but whose anticoagulant activities are reduced.

Nevertheless, as regards either non-fractionated heparins or low molecular weight heparin, the risk of haemorrhage remains the main complication of heparin-based treatments. As a result, there is a considerable limit on the use of heparins, which are contraindicated in particular in patients with a predisposition towards haemorrhaging, patients suffering from duodenal or gastric ulcers or alternatively patients who have recently undergone a surgical intervention, in whom antithrombotic treatment with heparin may lead to haemorrhaging.

Consequently, the advantageous properties of heparins, namely their antithrombotic or anticoagulant activity, cannot be correctly exploited on account of their considerable side effects associated with this permanent risk of haemorrhaging.

When haemorrhages occur during treatments with heparin, the treatment makes use of protamine sulphate which brings about the in vivo neutralization of the heparin.

Although protamine has been used in this way for many years, the mechanism by which heparin is neutralized by protamine is not well known. A relatively recent study has shown simply that low molecular weight heparins were neutralized to a lesser degree than non-fractionated heparins ("In Vitro Protamine Neutralization Profiles of Heparine Differing in Source and Molecular Weight", SEMINARS IN THROMBOSIS AND IN HEMOSTASIS, vol. 15 No. 4, 1989).

The problem which the present invention aims to solve is thus one of reducing the considerable risk of haemorrhaging outlined above, which limits the therapeutic use of heparins.

The aim of the invention is, more precisely, to eliminate the risk of haemorrhaging associated with heparins as much as possible while at the same time retaining their main properties, in particular the antithrombotic activity.

Thus, the aim of the present invention is to provide heparin compositions which have very advantageous pharmacological properties, in particular antithrombotic properties, which are essentially equivalent to those of the heparins used hitherto, without therewith exhibiting the major drawback which lies in the considerable risk of haemorrhaging.

Another aim of the present invention is also to provide a process for the preparation of such compositions which is simple to carry out and inexpensive, moreover allowing their therapeutic applications to be developed.

The invention is also directed towards the therapeutic applications of these compositions.

These aims are achieved using heparin compositions according to the invention which have antithrombotic activity and are substantially free of haemorrhagic activity. These compositions are characterized by the fact that they consist essentially of heparin fractions as obtained by the in vitro neutralization of heparin with protamine.

The expression heparin fraction neutralized with protamine is understood to refer to any fraction derived from a native or already fractionated heparin, or from a synthetic heparin, whose haemorrhagic power has been neutralized by the action of protamine or any analogue or equivalent thereof having a similar capacity to reduce the haemorrhagic power.

The compositions according to the invention advantageously consist of heparin fractions as obtained by the in vitro neutralization of a non-fractionated heparin or of a low molecular weight heparin, with protamine.

According to one embodiment of the invention, the composition consists of heparin fractions, 25% of which have a molecular mass of less than 2.5 kDa and 40% of which have a molecular mass of greater than 20 kDa.

According to another embodiment of the invention, the composition consists solely of heparin fractions having a molecular mass of less than 2.5 kDa.

In other embodiments the heparin fractions have a molecular mass spectrum which depends on the modes of neutralization with protamine that are used.

The compositions in accordance with the invention are substantially free of protamine.

The invention also provides a process for the preparation of the abovementioned compositions, characterized in that it comprises a step of in vitro neutralization of heparin with protamine.

The inventors have discovered, surprisingly, that the haemorrhagic activity of heparin can be neutralized in vitro, in particular using protamine, while at the same time retaining its antithrombotic properties.

More precisely, the process according to the invention consists in reacting, in solution, a heparin with protamine, in particular in the form of a protamine salt, according to variable heparin/protamine ratios.

According to a preferred embodiment of the invention, a heparin solution is mixed with a solution of protamine salt, preferably at room temperature, the mixture obtained is centrifuged and the supernatant is collected.

According to the invention, the term heparin solution refers to a solution of native or already fractionated heparin, or of synthetic heparin.

The protamine salt advantageously consists of protamine sulphate.

According to the invention, any protamine analogue or equivalent which has a similar capacity to neutralize heparin and thus to reduce the haemorrhagic power can be used.

The supernatant may then be freeze-dried.

The heparin to be treated and the protamine may be used in different ratios which lead essentially to elimination of the risk of haemorrhaging which is associated with heparins.

The process comprises the step of neutralizing a heparin with protamine or an equivalent, preferably in heparin/protamine proportions of from 2/1 to 1/2.

According to one embodiment of this process, the heparin/protamine ratio is about 1/1. In this case, heparin compositions comprising fractions, at least 25% of which have a molecular mass of less than 2.5 kDa and at least 40% of which have a molecular mass of greater than 20 kDa, are obtained.

According to another embodiment of the invention, the heparin/protamine ratio is about 1/2. In this case, heparin compositions essentially comprising fractions having a molecular mass of less than 2.5 kDa are obtained.

According to the process in accordance with the present invention, protamine-free heparin compositions are obtained.

Pharmacological study of the heparin compositions of the invention has made it possible to demonstrate, surprisingly, that they are substantially free of haemorrhagic activity and, in parallel, retain their antithrombotic property.

This pharmacological study also demonstrated, surprisingly, that the heparin fractions obtained by neutralization with protamine in accordance with the invention exert antithrombotic activity which increases as the doses administered increase, without increasing in parallel their haemorrhagic or anticoagulant activity.

Another experimental procedure made it possible to show that the compositions according to the invention are capable of inhibiting the hydrolytic activity of human leucocyte elastase more effectively than non-fractionated heparin. The suppression of the risk of haemorrhaging, in accordance with the invention, makes it possible to envisage administration via a parenteral route or via a broncho-pulmonary route as an aerosol, in the treatment of certain broncho-pulmonary complaints which may involve an excess of leucocyte elastase, such as acute respiratory distress syndromes, mucoviscidosis, and obstructive chronic bronchopneumopathies.

The heparin compositions according to the invention, which are stable and non-toxic, may be employed for the preparation of medicaments which are useful in various therapeutic applications. These applications are those of heparin and of its standard derivatives, including cases where heparin is contraindicated on account of the risk of haemorrhaging which the patient presents. They may serve in particular for the preparation of medicaments for the treatment and prevention of venous or arterial thromboses or alternatively for preventing the activation of coagulation in extracorporeal circulation.

The invention thus relates also to pharmaceutical compositions comprising a therapeutically effective amount of a heparin composition according to the invention as described above, in combination with a pharmaceutically acceptable vehicle.

These may be, for example, antithrombotic pharmaceutical compositions or alternatively compositions for inhibiting the hydrolytic activity of human leucocyte elastase.

The heparin fractions of these compositions may be placed in the form of a pharmaceutically acceptable salt according to standard processes.

The pharmaceutical compositions according to the invention are advantageously injectable formulations intended in particular for parenteral administration.

For other applications, such as the inhibition of leucocyte elastase, formulations which are suitable for broncho-pulmonary administration are advantageously provided.

Other characteristics and advantages of the invention will become apparent on reading the examples given below by way of non-limiting guide, with reference to the attached drawings, in which.

EXAMPLES

Figure 1:
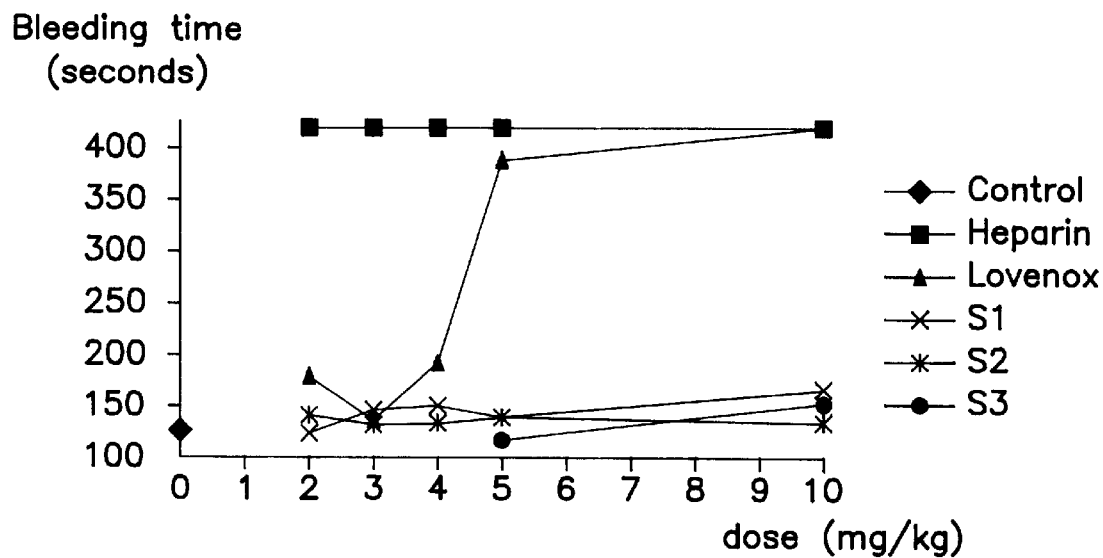
FIG. 1 is a comparative graph of the haemorrhagic activity of non-fractionated heparin, of low molecular weight and non-haemorrhagic heparin of the heparin compositions according to the invention (S1, S2, S3)

Products used: standard heparin (LEO), protamine sulphate (CHOAY) and low molecular weight heparin, "Enoxaparine", marketed under the name "Lovenox" (PHARMUKA).

EXAMPLE 1

Preparation of Supernatant S1

14.4 ml of a standard heparin solution having a titre of 72,000 IU (480 mg) and 48 ml of a protamine sulphate solution having a titre of 48,000 HAU are prepared. These solutions are mixed together at room temperature. The heparin/protamine ratio is then 1:1, that is to say that 1 mg of heparin is neutralized with 1 mg of protamine sulphate.

The mixture thus obtained is centrifuged for 10 minutes and the supernatant is recovered and freeze-dried.

EXAMPLE 2

Preparation of the Supernatant S2

The process is carried out as described in Example 1, using 9 ml of a standard heparin solution (i.e. 45,000 IU, 300 mg) and 60 ml of protamine sulphate (i.e. 60,000 HAU). The heparin/protamine ratio is then 1/2, that is to say that 1 mg of heparin is neutralized with 2 mg of protamine sulphate.

EXAMPLE 3

Preparation of the Supernatant S3

The process is performed as described in Example 1, using 4 ml of a solution of low molecular weight heparin, "Enoxaparine" (Lovenox), (i.e. 400 mg) and 40 ml of protamine sulphate (i.e. 40,000 HAU). The heparin/protamine ratio is then 1/1, that is to say that 1 mg of low molecular weight heparin is neutralized with 1 mg of protamine sulphate.

BIOLOGICAL CHARACTERIZATION

Molecular mass distribution

TABLE I

Supernatant S1 obtained according to Example 1 - Molecular mass distribution expressed as a percentage

| Molecular mass | UV | RI |
|---|---|---|
| >20 kDa | 43.3 | 47.3 |
| 16–20 kDa | 2.7 | 4.45 |
| 12–16 kDa | 4.5 | 7.65 |
| 8–12 kDa | 9.7 | 13.85 |
| 5–8 kDa | 8.13 | 11.8 |
| 2.5–5 kDa | 6.36 | 10.3 |
| <2.5 kDa | 25.16 | 4.65 |
| | Σ = 99.85 | Σ = 100 |

TABLE II

Supernatant S2 obtained according to Example 2 - Molecular mass distribution expressed as a percentage

| Molecular mass | UV | RI |
|---|---|---|
| >20 kDa | 0 | 0 |
| 16–20 kDa | 0 | 0 |
| 12–16 kDa | 0 | 0 |
| 8–12 kDa | 0 | 0 |
| 5–8 kDa | 0 | 0 |
| 2.5–5 kDa | 0 | 0 |
| <2.5 kDa | 100 | 100 |
|  | $\Sigma = 100$ | $\Sigma = 100$ |

Ultraviolet absorption spectrum for the supernatant S1 (Example 1)

A solution diluted to 1/20 shows two absorption peaks at the following wavelengths:

212 nm: OD=3.47 and 271.5 nm: OD=2.22

Titration of the supernatant S1 (Example 1)

Before freeze-drying the supernatant S1 prepared according to Example 1, each flask contains 0.7 ml of supernatant solution. 12 identical assays were carried out in order to check the reproducibility: the results are given in Table III below:

TABLE III

| FLASK No. | Mass of heparin per flask (mg/0.7 ml) | AZURE A (IU/mg/ml) | A-Xa (IU/mg/ml) | A-IIa (IU/mg/ml) |
|---|---|---|---|---|
| 1 | 23.43 | 84 | 61 | 32 |
| 2 | 23.43 | 83 | 54 | 29 |
| 3 | 22.41 | 84 | 62 | 32 |
| 4 | 22.53 | 83 | 58 | 30 |
| 5 | 23.50 | 86 | 63 | 30 |
| 6 | 24.20 | 83 | 56 | 28 |
| 7 | 21.70 | 86 | 62 | 29 |
| 8 | 23.30 | 83 | 61 | 31 |
| 9 | 22.00 | 85 | 63 | 30 |
| 10 | 20.70 | 83 | 58 | 32 |
| 11 | 21.30 | 85 | 57 | 28 |
| 12 | 20.80 | 80 | 54 | 30 |
| M ± DS | 22 ± 1.2 | 84 ± 2.2 | 59 ± 3.3 | 30 ± 1.4 |

AZURE A: Method of Klein M.D. et al.
A-Xa: Chronometric assay of the heparin (Hépadot Laboratoire Stago)
A-IIa: Aminolytic method
- Protein assay
The proteins in the supernatants S1 and S2, prepared according to Examples 1 and 2 respectively, are assayed according to the Pierce method (Pierce Laboratory reagent kit).

The results are given in Table IV below:

TABLE IV

| SOLUTIONS | PROTEIN CONCENTRATIONS (µg/ml) |
|---|---|
| S1 (2 mg/ml) | 3.2 |
| S1 (1 mg/ml) | <1 |
| S2 (2 mg/ml) | 29.9 |
| S2 (1 mg/ml) | 11.2 |
| LOVENOX (2 mg/ml) | 8.6 |
| LOVENOX (1 mg/ml) | 6.7 |

Electrolyte composition (mEq/l)

The electrolyte composition of the supernatants S1 and S2 is given in Table V below:

TABLE V

|  | Na | K |
|---|---|---|
| S1 | 24 | 0.55 |
| S2 | 18 | 0.21 |

Determination of the pH

TABLE VI

| Solutions | pH |
|---|---|
| S1 | 5.57 |
| S2 | 4.52 |

PHARMACOLOGICAL STUDY

A. Experimental studies in rats in a model of venous thrombosis induced by stasis and a model of induced haemorrhage:

Studies were carried out according to the method described by C. Doutremepuich et al., "Experimental venous thrombosis in rats treated with heparin and a low molecular weight heparin fraction", Haemostasis, 13, 109–112 (1983).

a. Curative model (subcutaneous injections two hours after induction of the thrombosis).

Two studies were carried out according to the following procedure:

T0: ligation of the vena cava

T0+2H: subcutaneous injection of the solutions

T0+5H30: induction of the haemorrhage

T0+6H: samples taken (blood and clot)

The results obtained after the first study are collated in Tables VII and VIII below:

TABLE VII

|  | Weight of clot (mg) | IHT (sec) | CKT (sec) | DTT (sec) |
|---|---|---|---|---|
| Control | 5.54 ± 1.54 | 108 ± 20 | 19.6 ± 1.3 | 19.4 ± 0.5 |
| Heparin (2 mg) | 1.76 ± 0.53* | 420 ± 00* | 180.0 ± 0* | 180.0 ± 0* |
| S1 (2 mg) | 2.90 ± 0.88* | 141 ± 36 | 23.2 ± 1.8 | 20.5 ± 1.5 |
| S2 (2 mg) | 4.19 ± 1.07 | 123 ± 32 | 21.4 ± 2.1 | 19.6 ± 1.4 |
| Lovenox (2 mg) | 3.03 ± 0.72* | 153 ± 48 | 25.2 ± 2.1 | 20.8 ± 0.9 |
| Heparin (1 mg) | 4.18 ± 1.06 | 144 ± 60 | 25.9 ± 2.6 | 21.5 ± 1.0 |
| S1 (1 mg) | 4.68 ± 0.91 | 122 ± 28 | 23.1 ± 1.7 | 20.5 ± 1.5 |
| S2 (1 mg) | 4.55 ± 1.48 | 123 ± 34 | 21.3 ± 2.1 | 19.7 ± 1.2 |
| Lovenox (1 mg) | 4.84 ± 0.94 | 146 ± 40 | 21.6 ± 2.0 | 20.0 ± 1.5 |

IHT: Induced haemorrhage time
CKT: Cephalin kaolin time
DTT: Dilute thrombin time
* = p < 0.05 (Mann Whitney test)

TABLE VIII

|  | Platelets ($\times 10^9$/l) | White corpuscles ($\times 10^9$/l) | Red corpuscles ($\times 10^{12}$/l) |
|---|---|---|---|
| Control | 538 ± 220 | 5.70 ± 3.27 | 7.40 ± 0.39 |
| Heparin (2 mg) | 684 ± 241 | 4.25 ± 1.80 | 7.71 ± 1.06 |
| S1 (2 mg) | 589 ± 222 | 4.07 ± 2.06 | 7.61 ± 0.71 |
| S2 (2 mg) | 546 ± 155 | 4.61 ± 2.73 | 7.53 ± 0.97 |
| Lovenox (2 mg) | 606 ± 113 | 3.45 ± 1.98 | 7.81 ± 0.99 |
| Heparin (1 mg) | 692 ± 263 | 5.02 ± 3.25 | 7.71 ± 1.05 |
| S1 (1 mg) | 575 ± 200 | 4.23 ± 1.68 | 7.26 ± 0.39 |
| S2 (1 mg) | 600 ± 242 | 4.21 ± 2.70 | 7.46 ± 1.15 |
| Lovenox (1 mg) | 621 ± 188 | 5.47 ± 2.62 | 7.88 ± 0.81 |

This first study shows that heparin neutralized in vitro with protamine in a heparin/protamine ratio of 1/1 leading to the supernatant S1 exerts, at a dose of 2 mg, quite considerable antithrombotic activity which is comparable to that of non-neutralized heparin and to that of Lovenox (low molecular weight heparin), whereas the anticoagulant activity and the haemorrhagic activity are only weakly increased.

The supernatant S1 has no effect on the blood cells.

Moreover, the supernatant S2, obtained by neutralization according to a heparin/protamine ratio of 1/2, exerts no haemorrhagic activity but possesses reduced antithrombotic activity.

The results of the second study are given in Table IX below:

TABLE IX

| GROUPS |  | Clot wt. (mg) | IHT (s) | CKT (s) | DTT (s) |
|---|---|---|---|---|---|
| PLACEBO |  | 6.91 ± 1.09 | 126 ± 49 | 22 ± 1.8 | 19.6 ± 1.0 |
| 2 mg | HEPARIN | 3.41 ± 1.08* | >420* | >180* | >180* |
|  | SN1 | 5.22 ± 2.17 | 124 ± 58 | 21.2 ± 1.14 | 19.5 ± 1.3 |
|  | SN2 | 5.63 ± 1.93 | 145 ± 38 | 22.1 ± 2.80 | 20.0 ± 1.2 |
|  | LOVENOX | 4.33 ± 1.06* | 182 ± 56* | 24.9 ± 0.70 | 21.3 ± 1.3 |
| 3 mg | HEPARIN | 3.38 ± 0.55 | >420* | >180* | >180* |
|  | SN1 | 4.73 ± 1.77 | 151 ± 24 | 22.0 ± 1.6 | 19.5 ± 0.5 |
|  | SN2 | 5.26 ± 1.24 | 131 ± 47 | 20.4 ± 1.8 | 20.8 ± 1.8 |
|  | LOVENOX | 3.62 ± 0.90* | 140 ± 38* | 29.0 ± 1.6 | 22.0 ± 1.7 |
| 4 mg | HEPARIN | 2.75 ± 0.91 | >420* | >180* | >180* |
|  | SN1 | 4.09 ± 1.10 | 155 ± 43 | 22.5 ± 1.9 | 19.7 ± 0.9 |
|  | SN2 | 4.72 ± 2.33 | 136 ± 48 | 18.6 ± 5.7 | 19.2 ± 0.5 |
|  | LOVENOX | 3.33 ± 0.98 | 198 ± 76* | 50.9 ± 3.9* | 39.4 ± 1.9* |
| 5 mg | HEPARIN | 2.15 ± 0.83* | >420* | >180* | >180* |
|  | SN1 | 3.70 ± 1.28* | 142 ± 33 | 29.5 ± 3.6* | 24.2 ± 9.3 |
|  | SN2 | 4.84 ± 1.12 | 145 ± 48 | 22.0 ± 1.3 | 20.3 ± 0.7 |
|  | SN3 | 3.52 ± 0.30* | 121 ± 15 | 20.8 ± 1.8 | 19.6 ± 1.75 |
|  | LOVENOX | 2.85 ± 1.14* | 389 ± 86* | >180* | >180* |
| 10 mg | HEPARIN | 0.98 ± 0.82* | >420* | >180* | >180* |
|  | SN1 | 3.15 ± 1.21* | 171 ± 64* | 30.2 ± 2.5* | 32.6 ± 6.9* |
|  | SN2 | 4.09 ± 1.16* | 136 ± 74 | 23.8 ± 1.7 | 20.0 ± 0.7 |
|  | SN3 | 2.29 ± 0.40* | 157 ± 21 | 27.0 ± 2.0 | 23.0 ± 1.0 |
|  | LOVENOX | 1.44 ± 0.48* | >420* | >180* | >180* |

Clot wt.: Weight of the experimental clot
IHT: Induced haemorrhage time
CKT: Cephalin-kaolin time
DTT: Dilute thrombin time It is seen from the results obtained that the antithrombotic activity of fractions S1, S2 and S3 according to the invention increases as the doses administered increase.

If we refer to the dose-effect curves, established for doses ranging from 2 mg/kg to 10 mg/kg, it is seen, in FIG. 1, that irrespective of the type of heparin treated in accordance with the invention, the heparin fraction obtained has haemorrhagic activity similar to that of the control group, even at the highest doses. The non-fractionated heparin and the low molecular weight heparin (Lovenox), which is not neutralized with protamine, according to the invention, have considerable haemorrhagic activity when compared with the heparin fractions of the invention.

Figure 2:
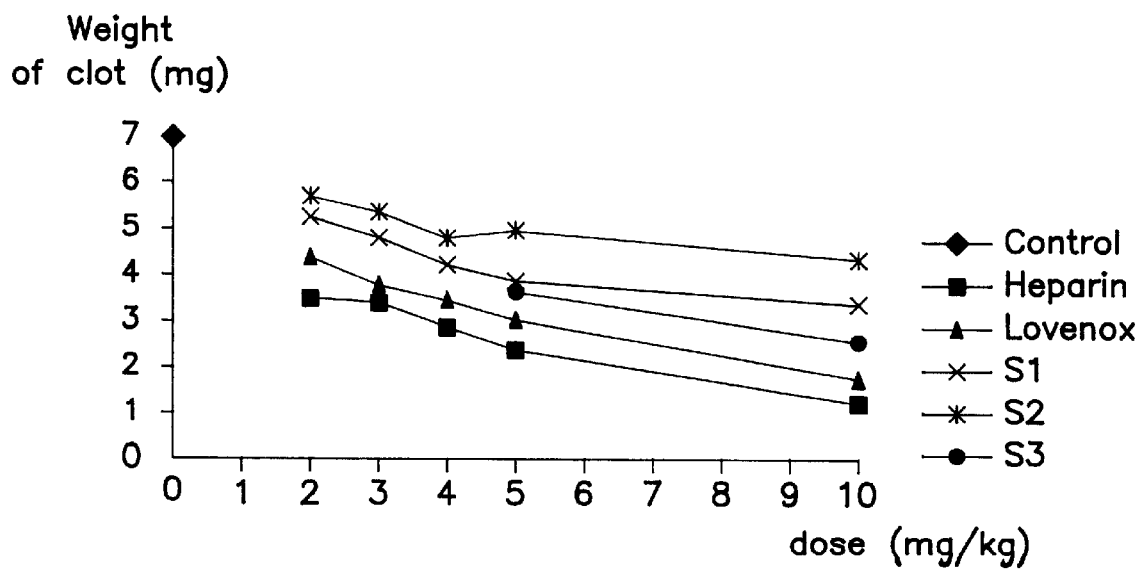
FIG. 2 is a comparative graph of the antithrombotic activity of non-fractionated heparin, of low molecular weight heparin and of heparin compositions according to the invention (S1, S2, S3).

FIG. 2 shows that the heparin fractions obtained according to the invention have advantageous antithrombotic activity. In the case of fraction S1 (heparin/protamine ratio of 1/1), this activity is comparable to that of non-neutralized heparins in accordance with the invention.

b. Preventive model (subcutaneous administration one hour before induction of the thrombosis).

The study was carried out with the supernatant S1 (Example 1) according to the following procedure:

T0: subcutaneous injection of the solutions
T0+1 hour: induction of the stasis
T0+24 hours: samples taken (blood and clot)

The results obtained are given in Table X below:

TABLE X

|  | Weight of clot (mg) | CKT (sec) | DTT (sec) | Ti (sec) |
|---|---|---|---|---|
| Control | 5.13 ± 1.03 | 19.5 ± 0.4 | 18.7 ± 0.6 | 19.8 ± 0.83 |
| Heparin (4 mg) | 3.40 ± 0.70* | 20.7 ± 0.4 | 19.3 ± 0.8 | 19.8 ± 1.30 |

TABLE X-continued

|  | Weight of clot (mg) | CKT (sec) | DTT (sec) | Ti (sec) |
|---|---|---|---|---|
| S1 (4 mg) | 3.23 ± 0.61* | 20.5 ± 1.1 | 19.4 ± 0.8 | 19.3 ± 0.83 |
| Lovenox (4 mg) | 3.48 ± 0.94* | 19.6 ± 0.8 | 19.7 ± 0.9 | 19.7 ± 1.09 |

CKT: Cephalin kaolin time
DTT: Dilute thrombin time
Ti: Titrarin (Stago Laboratory) time
* = p < 0.05 (Mann Whitney test)

The results obtained show that, for preventive purposes, S1 exerts antithrombotic activity which is comparable to that of heparin and Lovenox, 24 hours after induction of the thrombosis.

B. Experimental study in rats in a model of thrombosis induced by generation of free radicals (reference: Doutremepuich—In press—Annales de Cardiologie et Angiologie)

The study was carried out with S1 (Example 1) according to the following procedure:

(T0: subcutaneous injection of the solutions)

T0+25 min: injection of rose bengal at a dose of 5 mg/kg

T0+30 min: induction of free radicals in the first arteriole by photochemical reaction T0:55 min: injection of rose bengal at the same dose T0+60 min: induction of free radicals in the second arteriole T0+85 min: injection of rose bengal at the same dose T0+90 min: induction of free radicals in a venule.

After the final thrombosis, a blood sample is taken intracardially.

The excitation time is set at 2 minutes and the observation time at 10 minutes.

The results given in Table XI below are obtained:

TABLE XI

|  | CONTROL | S1 (2 mg/kg) | HEPARIN (2 mg/kg) |
|---|---|---|---|
| Arteriole | T0 + 30' | | |
| Duration of embolization (min) | 4.50 ± 0.82 | 9.68 ± 0.44* | 6.80 ± 2.32 |
| Number of emboli | 12.00 ± 2.45 | 4.00 ± 3.56* | 3.56 ± 2.12* |
| Arteriole | T0 + 60' | | |
| Duration of embolization (min) | 3.49 ± 0.36 | 9.81 ± 0.25* | 5.9 ± 3.6 |
| Number of emboli | 7.33 ± 0.47 | 5.00 ± 2.45 | 4.56 ± 3.6 |
| Venule | T0 + 90' | | |
| Duration of embolization (min) | 4.53 ± 2.04 | 3.68 ± 2.06 | — |

TABLE XI-continued

|  | CONTROL | S1 (2 mg/kg) | HEPARIN (2 mg/kg) |
|---|---|---|---|
| Number of emboli | 7.00 ± 4.32 | 4.00 ± 1.41* | — |

Duration of embolization: time between the first embolus and the final embolus detaching from the clot.

Number of emboli: number of emboli detaching from the clot.

In this model of thrombosis induced by free radicals, the supernatant S1 (Example 1) exerts significant antithrombotic activity when compared with the placebo group, which persists after 90 minutes (T0+90 min). This activity is higher than that of heparin injected at the same dose, after 30 and 60 minutes (T0+30 and T0+60 min).

C. Experimental study in rats in a model of thrombosis induced by endothelial lesion with a laser (Ref.: Vesvres, Haemostasis 1993, 23, 8–12).

a. Study 1

The study was carried out according to the following procedure:

T0: subcutaneous injection of the test substance at a dose of 2 mg/kg.

T0+35 min: induction of the arterial thrombosis using a laser beam.

The observation time is set at 10 minutes.

The results obtained are given in Table XII below:

TABLE XII

| | T0 + 35' (ARTERIAL THROMBOSIS) | | |
|---|---|---|---|
|  | CONTROL | S1 (2 mg/kg) | HEPARIN (2 mg/kg) |
| Number of laser strikes | 1.2 ± 0.4 | 2.0 ± 1.4 | 2.5 ± 3.3 |
| Number of emboli | 10.2 ± 2.7 | 1.5 ± 0.7* | 3.3 ± 2.4* |
| Duration of embolization (min) | 6.3 ± 1.8 | 1.0 ± 0.0* | 2.1 ± 1.8* |

S1 exerts antithrombotic activity comparable to that of non-neutralized heparin injected at the same dose and reduces the number of emboli as well as the duration of embolization in a statistically significant manner.

b. Study 2

The study was carried out according to the following procedure:

T0: subcutaneous injection of the test substances at a dose of 2 mg/kg.

T0+1 h: induction of the first arterial thrombosis

T0+3 h: induction of the second arterial thrombosis

T0+6 h: induction of the third arterial thrombosis.

The observation time is set at 10 minutes.

The results obtained are given in Table XIII below:

TABLE XIII

|  | T0 + 1 h | | T0 + 3 h | | T0 + 6 h | |
| --- | --- | --- | --- | --- | --- | --- |
|  | S1 | Hep | S1 | Hep | S1 | Hep |
| Number of laser strikes | 1.6 ± 0.5 | 1.6 ± 0.5 | 2.0 ± 0.0 | 1.6 ± 0.5 | 1.6 ± 0.5 | 1.0 ± 0.0 |
| Number of emboli | 3.0 ± 1.0 | 5.0 ± 1.7 | 5.3 ± 3.5 | 6.7 ± 1.2 | 8.3 ± 3.0 | 7.5 ± 2.1 |
| Duration of embolization | 1.3 ± 0.5 | 2.6 ± 1.2 | 2.3 ± 1.5 | 3.0 ± 1.0 | 4.3 ± 2.4 | 3.0 ± 1.4 |

S1 exerts antithrombotic activity comparable to that of heparin which has not been neutralized with protamine.

In conclusion, the studies described above show that antithrombotic activity is observed in the three models of experimental thrombosis, namely the venous model induced by stasis, the model of arterial thrombosis induced by free radicals and the model of arterial thrombosis induced by endothelial lesion with a laser.

According to the invention, the heparin fraction obtained from a low molecular weight heparin, "Enoxaparine" (Lovenox), has higher antithrombotic activity than that of the same low molecular weight heparin not treated in vitro with protamine and also higher than that of fractions obtained from non-fractionated heparins not treated in vitro with protamine, while at the same time no longer presenting any risk of haemorrhaging.

The process according to the invention makes it possible, in a simple and inexpensive manner, to substantially eliminate the haemorrhagic activity of heparins while at the same time retaining their antithrombotic activity.

We claim:

1. A heparin composition having antithrombotic activity and reduced hemorrhagic activity as expressed by an Induced Hemorrhagic Time (IHT) which is decreased by at least ⅓ compared to unfactionated heparin, consisting essentially of a supernatant resulting from centrifugation of the in vitro neutralization mixture of a heparin solution with a protamine solution.

2. The composition of claim 1 wherein the supernatant consists of heparin fractions, at least 25% of which have a molecular weight of less than 2.5 kDa.

3. The composition of claim 2 wherein the supernatant consists of fractions, at least 40% of which have a molecular weight greater than 20 kDa.

4. The composition of claim 2 wherein the supernatant consists of fractions with a molecular weight of less than 2.5 kDa.

5. The composition of claim 4 wherein the supernatant consists of a fraction having the molecular mass distribution given in Table II.

6. The composition of claim 2 wherein the supernatant consists of a fraction having the molecular mass distribution given in Table I.

7. A pharmaceutical composition for inhibition of the hydrolytic activity of human leucocyte elastase consisting essentially of the composition of claim 1 and a pharmaceutically acceptable carrier in an amount effective to inhibit human leucocyte elastase.

8. Pharmaceutical composition according to claim 7, wherein the composition is in a form which is suitable for broncho-pulmonary administration.

9. A method of inhibiting the hydrolytic activity of human leucocyte elastase in warm-blooded animals comprising administering to a warm-blooded animal an effective amount of a heparin composition according to claim 1.

10. The method of claim 9 wherein the heparin composition is administered by broncho-pulmonary route.

11. The composition of claim 1 wherein the heparin is unfractionated.

12. The composition of claim 1 wherein the heparin is a low molecular weight heparin.

13. A process for the preparation of the composition of claim 1 consisting essentially of contacting a heparin solution and a protamine salt solution to effect in vitro neutralization of heparin, centrifuging the resulting mixture and recovering the supernatant.

14. The process according to claim 13, wherein the protamine salt is protamine sulphate.

15. The process according to claim 13, wherein the heparin and the protamine are used in a ratio of 1 to 1.

16. The process according to claim 13, wherein the heparin and the protamine are used in a ratio of 1 to 2.

17. The process according to claim 13, wherein non-fractionated heparin is neutralized.

18. The process according to claims 13, wherein low molecular weight heparin is neutralized.

19. A method of inducing antithrombotic activity in warm-blooded animals comprising administering to a warm-blooded animal an antithrombotically effective amount of a composition of claim 1 which has reduced hemorrhagic activity and a pharmaceutically acceptable carrier in an amount effective to inhibit human leucocyte elastase.

20. The method of claim 19 wherein the heparin composition is administered by injection.

21. A pharmaceutical composition consisting essentially of an antithrombotically effective amount of the composition of claim 1 and a pharmaceutically acceptable vehicle.

22. The pharmaceutical composition of claim 21 in the form of an injectable solution.

* * * * *